United States Patent
Gilbert et al.

(10) Patent No.: US 10,806,822 B2
(45) Date of Patent: Oct. 20, 2020

(54) USE OF LIPIDS FOR PREVENTING FRETTING CORROSION IN THE MODULAR TAPERS OF ORTHOPEDIC IMPLANTS

(71) Applicants: Jeremy L. Gilbert, Mt. Pleasant, SC (US); David Pierre, Clemson, SC (US)

(72) Inventors: Jeremy L. Gilbert, Mt. Pleasant, SC (US); David Pierre, Clemson, SC (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 16/019,844

(22) Filed: Jun. 27, 2018

(65) Prior Publication Data

US 2019/0009002 A1 Jan. 10, 2019

Related U.S. Application Data

(60) Provisional application No. 62/525,253, filed on Jun. 27, 2017.

(51) Int. Cl.
| | |
|---|---|
| *A61L 27/28* | (2006.01) |
| *A61F 2/36* | (2006.01) |
| *A61L 27/34* | (2006.01) |
| *A61L 27/50* | (2006.01) |
| *A61L 27/06* | (2006.01) |
| *A61F 2/30* | (2006.01) |

(52) U.S. Cl.
CPC ............ *A61L 27/28* (2013.01); *A61F 2/3609* (2013.01); *A61L 27/06* (2013.01); *A61L 27/34* (2013.01); *A61L 27/50* (2013.01); *A61F 2002/30107* (2013.01); *A61F 2002/30332* (2013.01); *A61F 2002/30685* (2013.01); *A61F 2002/30718* (2013.01); *A61F 2002/365* (2013.01); *A61F 2002/3625* (2013.01)

(58) Field of Classification Search
None
See application file for complete search history.

(56) References Cited

U.S. PATENT DOCUMENTS

| | | | |
|---|---|---|---|
| 2005/0283255 A1* | 12/2005 | Geremakis | A61F 2/4644 623/23.51 |
| 2007/0078516 A1* | 4/2007 | Emami | A61F 2/4014 623/19.14 |
| 2016/0158405 A1* | 6/2016 | Denyer | A61K 9/1271 424/450 |
| 2018/0311045 A1* | 11/2018 | Noel | A61F 2/32 |

FOREIGN PATENT DOCUMENTS

CN 201946783 U * 8/2011

* cited by examiner

*Primary Examiner* — Marcia L Watkins
(74) *Attorney, Agent, or Firm* — David L. Nocilly; George R. McGuire; Bond Schoeneck & King, PLLC

(57) ABSTRACT

The use of lipids in the taper junction or other metal on metal interface of a modular orthopedic implant to prevent fretting corrosion and increase the pull off load. The incorporation of lipids or a lipid-like substrate within the taper junction increases the onset load and decreases the amount of corrosion. The incorporation of lipids also increases the pull-off load necessary to separate the head from the neck. As a result, the use of lipids in the taper junction of an orthopedic implant should reduce the need for revisions of implants, such as such as knee and hip replacements, which are often needed because of fretting corrosion.

6 Claims, 15 Drawing Sheets

USE OF LIPIDS FOR PREVENTING FRETTING CORROSION IN THE MODULAR TAPERS OF ORTHOPEDIC IMPLANTS

CROSS REFERENCE TO RELATED APPLICATIONS

The present application claims priority to U.S. Provisional No. 62/525,253, filed on Jun. 27, 2017.

BACKGROUND OF THE INVENTION

1. Field of the Invention

The present invention relates to orthopedic implants and, more specifically, to the use of lipids to prevent fretting corrosion in the taper junctions of modular orthopedic implants.

2. Description of the Related Art

Beginning in the mid-to-late 1980s, orthopedic implant designs have incorporated modularity, where components are assembled intraoperatively by means of a self-locking conical taper junction and have since become state of the art in hip implant design. The modular element of these designs characteristically consists of a conical tapered interface about the neck region of the implant between a metallic alloy and an opposing surface (an alloy or ceramic component). Modularity provides an optimal combination of varying sizes, biomaterials and designs to better restore anatomy and function of the joint for patient specificity. The function also provides a means for surgeons, during initial implantation or revision surgery, to combine elements of an implant to best meet patient needs and deliver successful outcomes.

Adaptive conical tapers, which allow for intraoperative adjustability are used to increase implant performance and the ease of component replacement during revision surgery. During revision surgery, the femoral head can be removed and replaced, limiting the invasive nature of the surgery and allowing a well-fixed femoral stem to remain. Taper modularity also allows the use of various head components differing in material and size, a surgical advantage which enables the prosthetic to be tailored to the patient.

Taper modularity, though advantageous, enables a variety of disadvantages. The flexible nature of the neck region allows an added motion during loading which can lead to micromotion about the interface. Micromotion on metallic surfaces can cause fretting and increased corrosion as a result (fretting corrosion). These modes of damage can generate metallic and metal-oxide corrosion-wear debris and these products have been associated with adverse local tissue reactions. The persistent effects of micromotion and corrosion over time can cause crevice corrosion, pitting and potential crack propagation which can cause pain to the patient and a need for revision.

BRIEF SUMMARY OF THE INVENTION

The present invention comprises the use of lipids in the taper junction or other metal on metal interface of modular orthopedic implants, such as knee and hip replacements. More specifically, the incorporation of lipids or a lipid-like substrate within the taper junction increases the onset load and decreases the amount of corrosion. The incorporation of lipids also increases the pull-off load necessary to separate the head from the neck.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
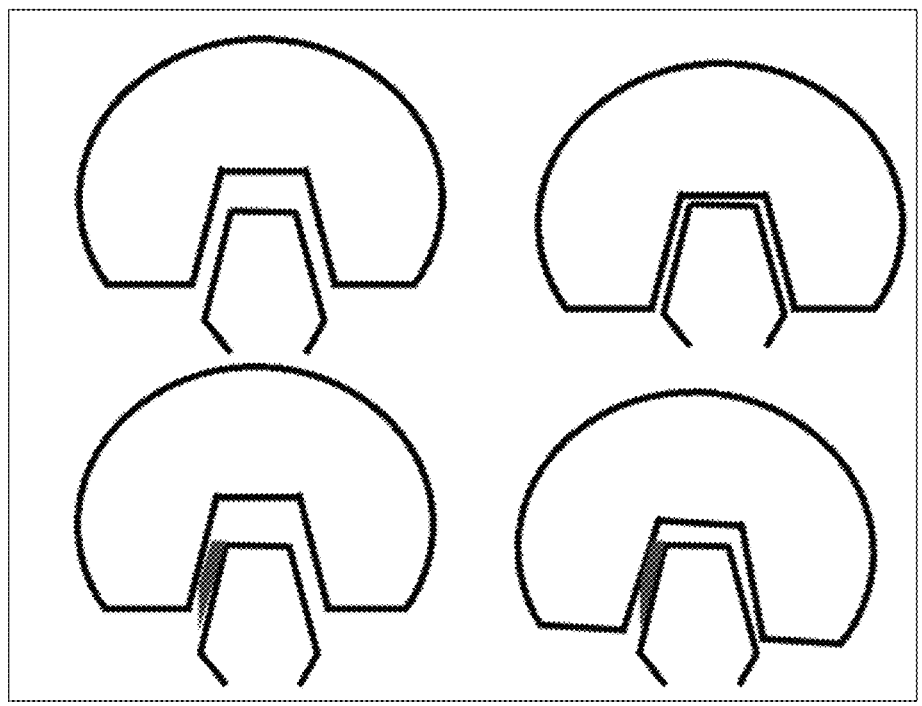
Figure 5:
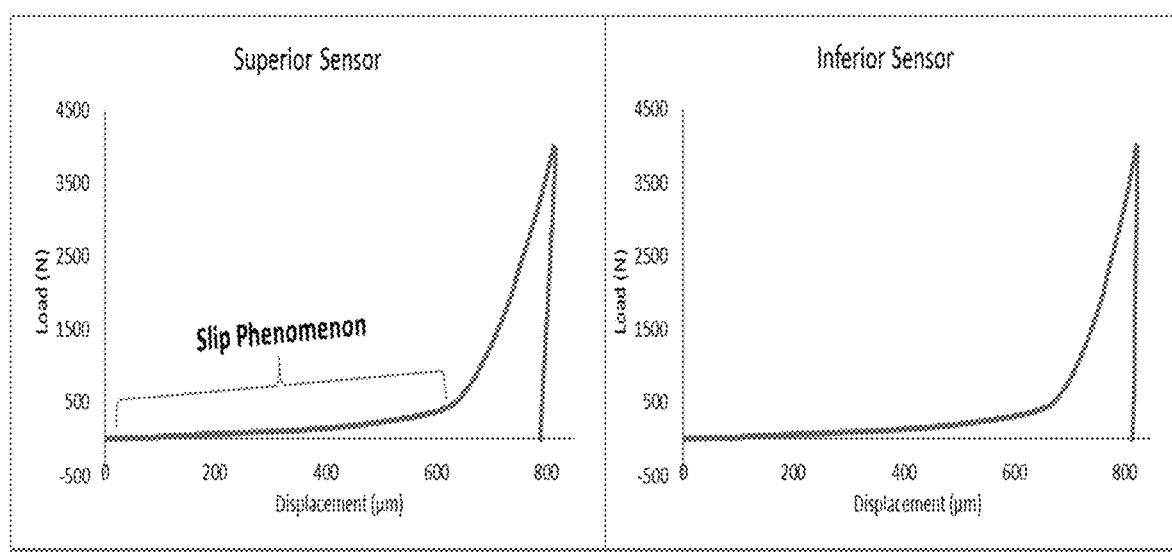
Figure 6:
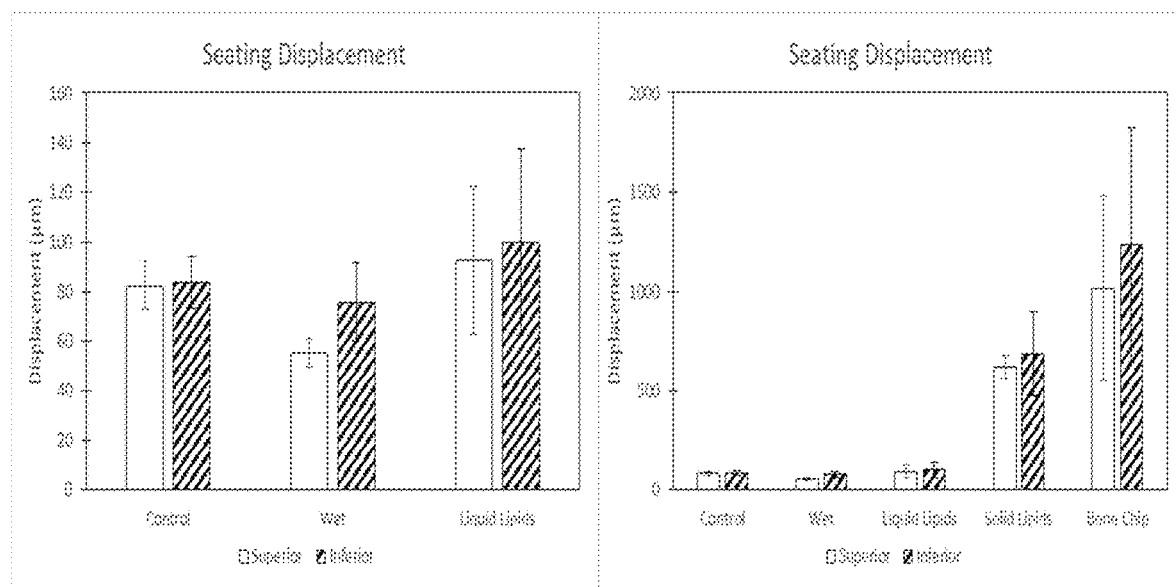
Figure 7:
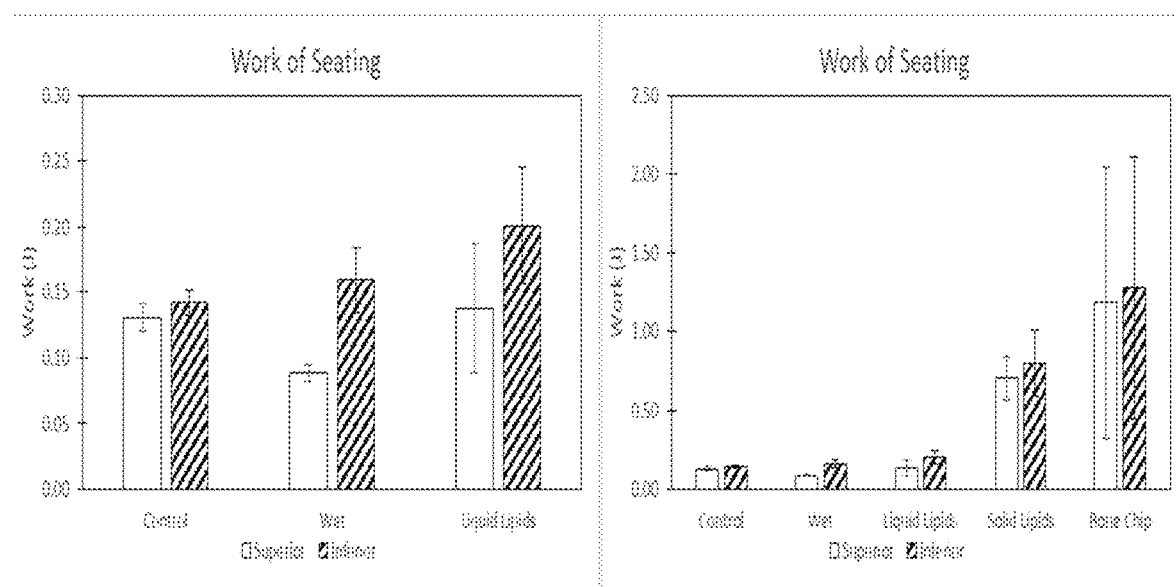
Figure 8:
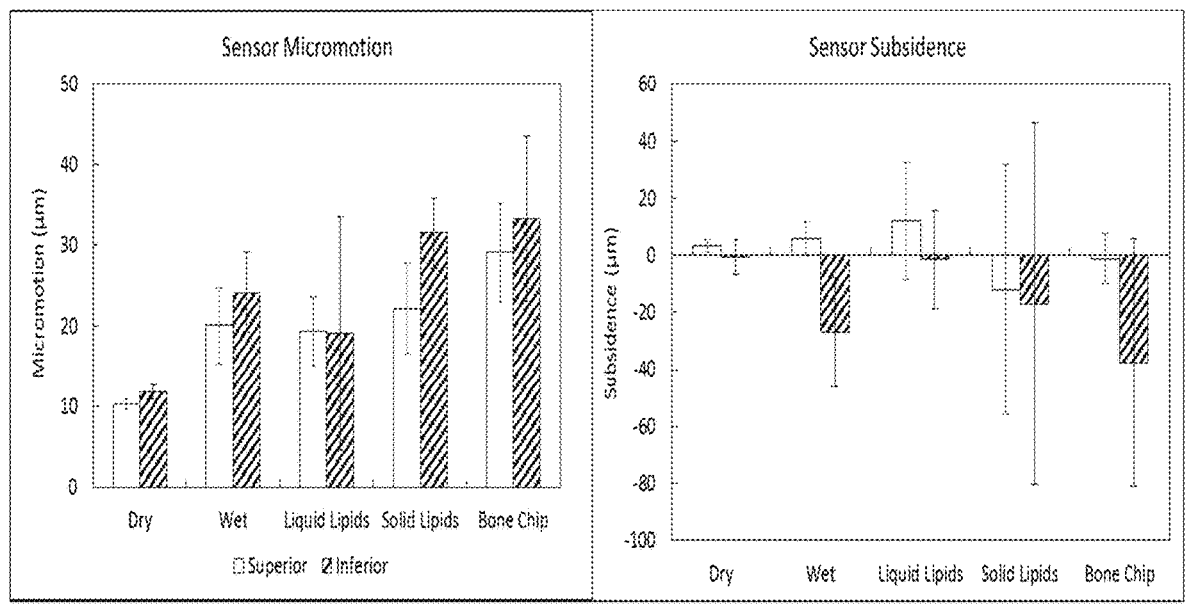
Figure 9:
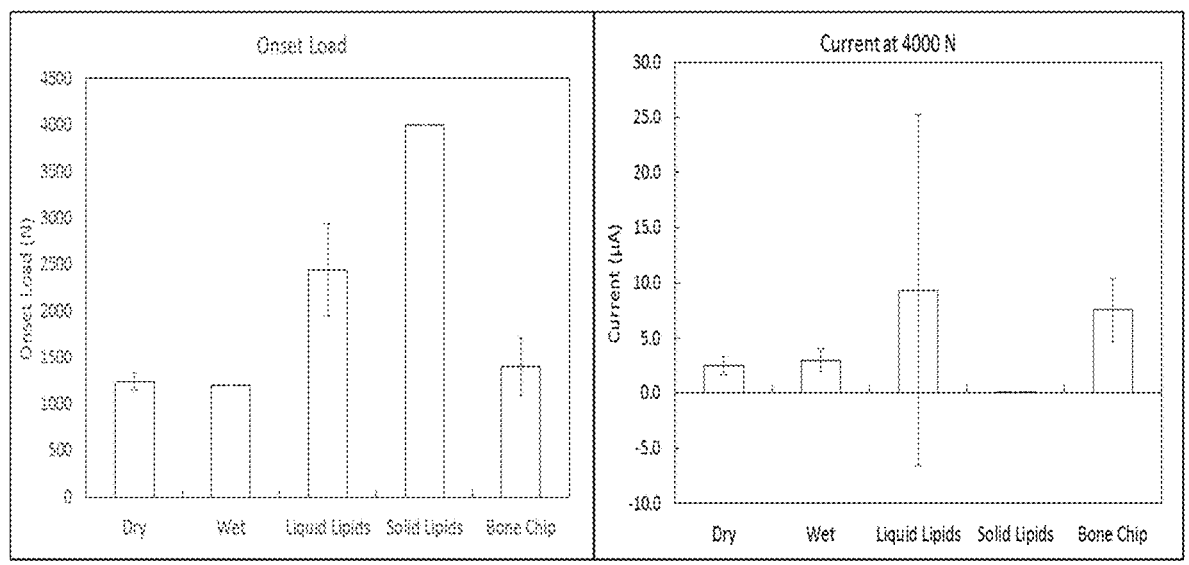
Figure 10:
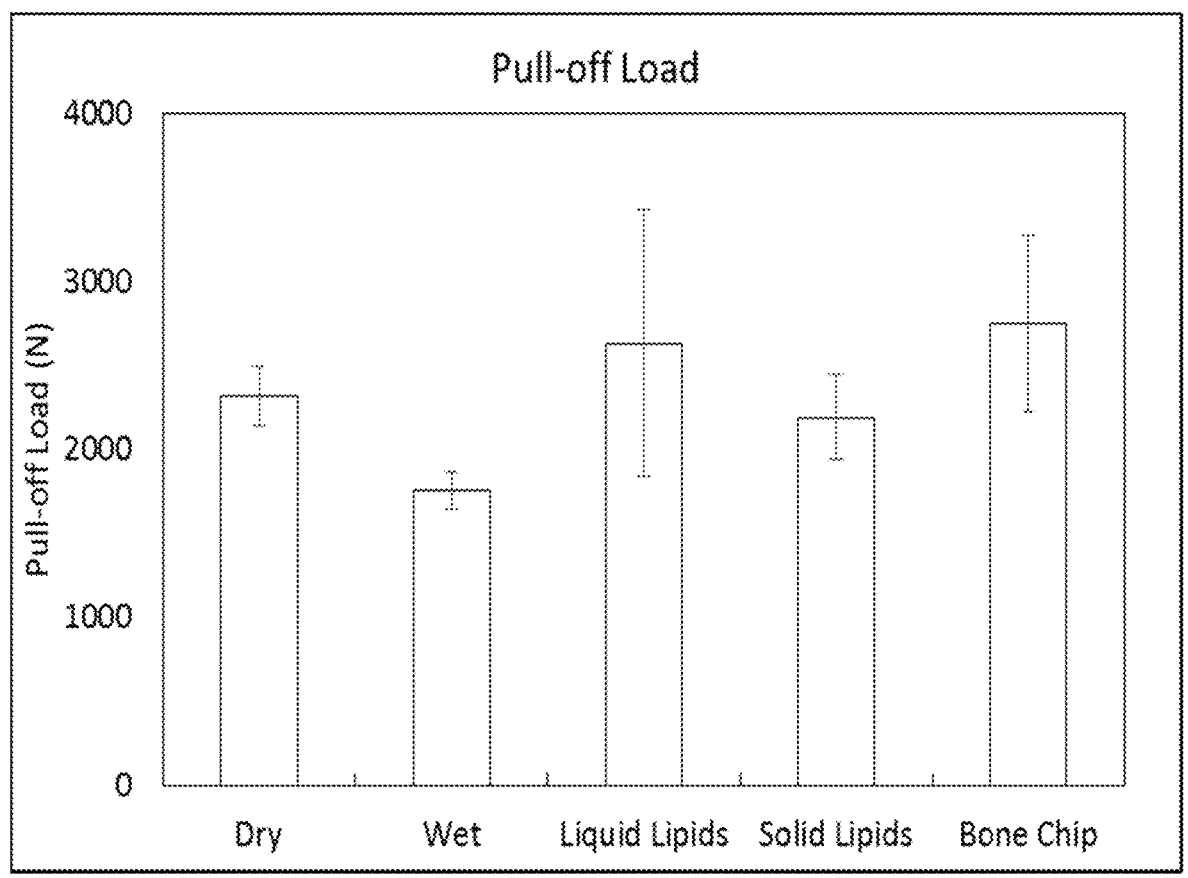
Figure 11:
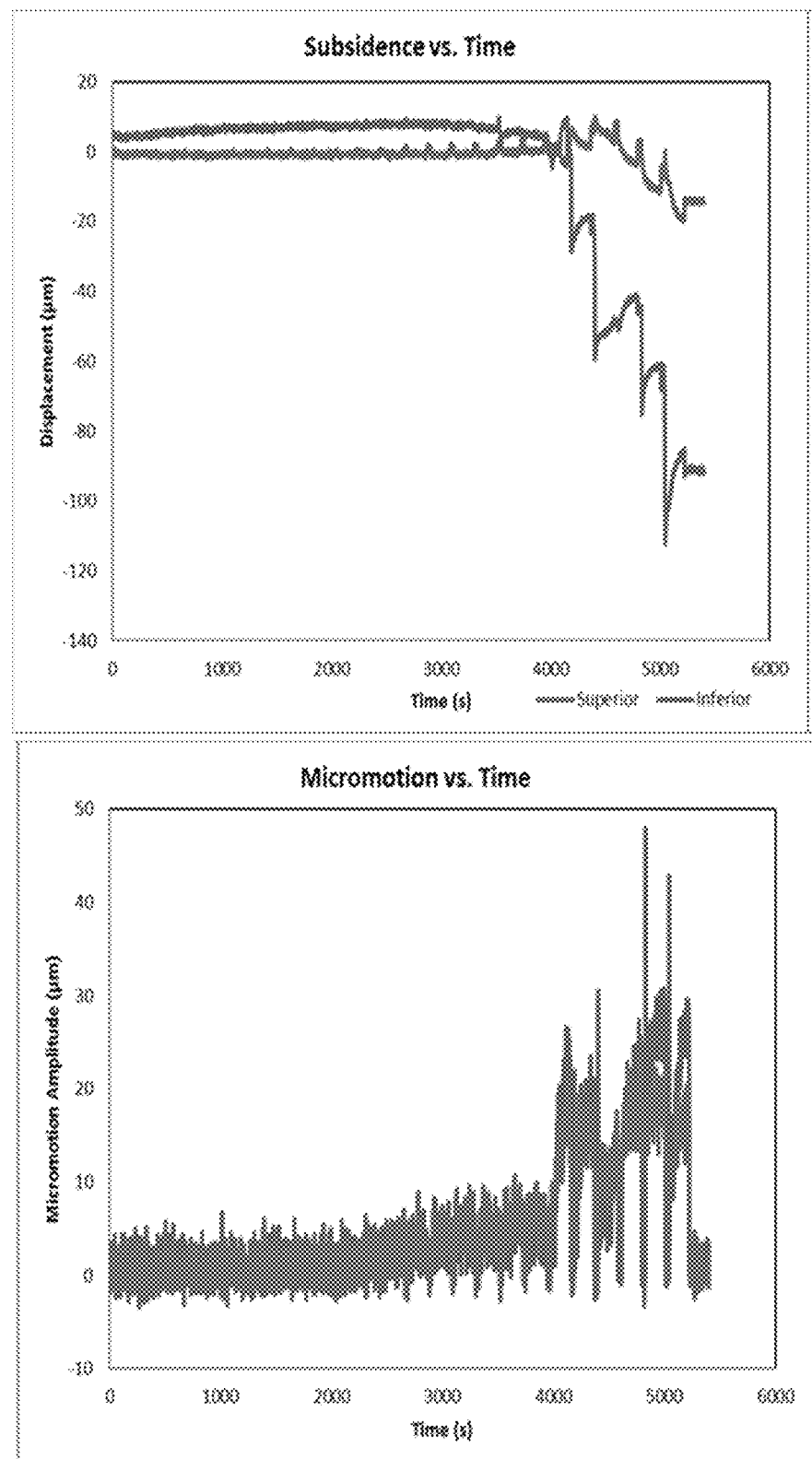
Figure 12:
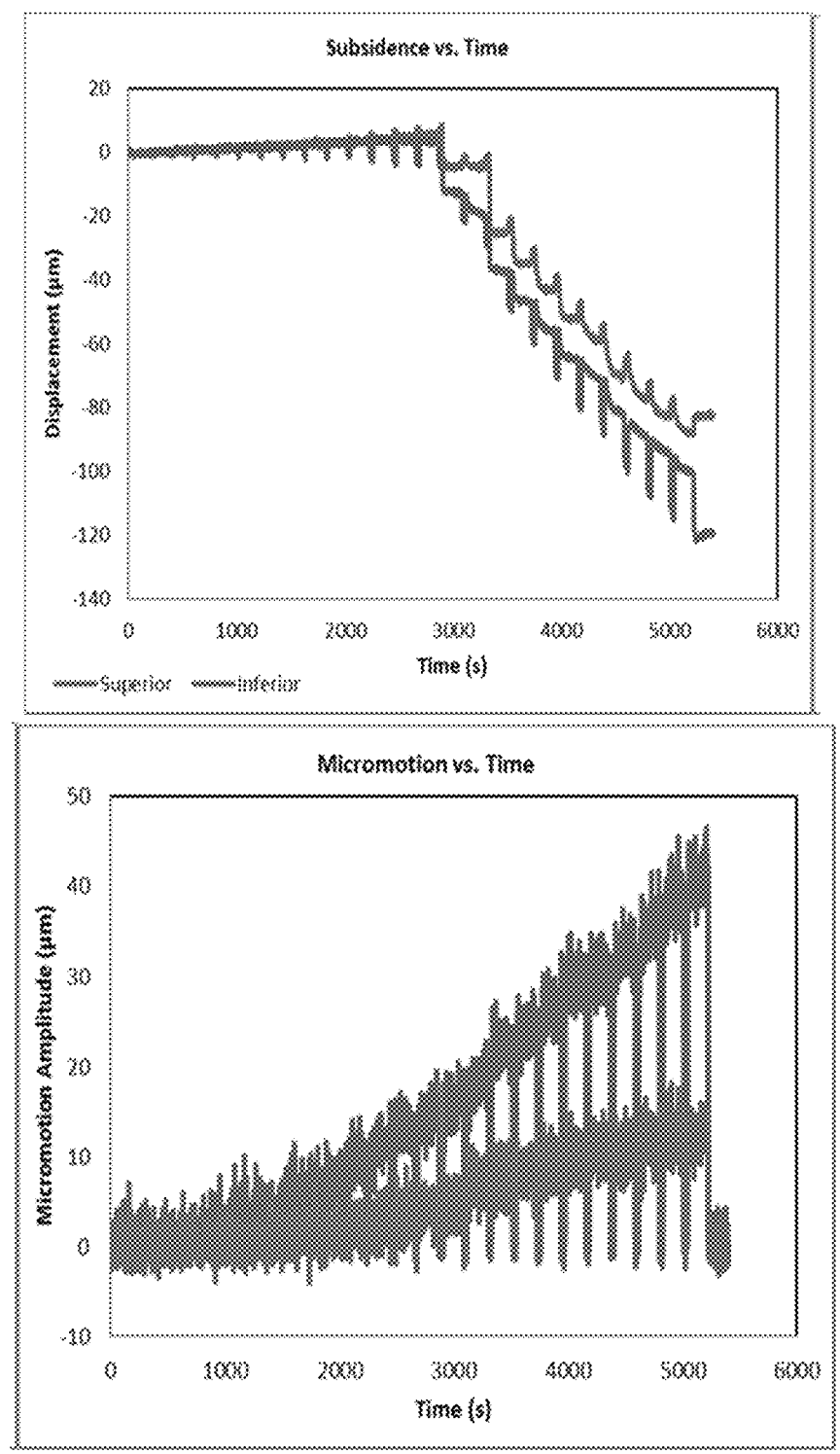
Figure 13:
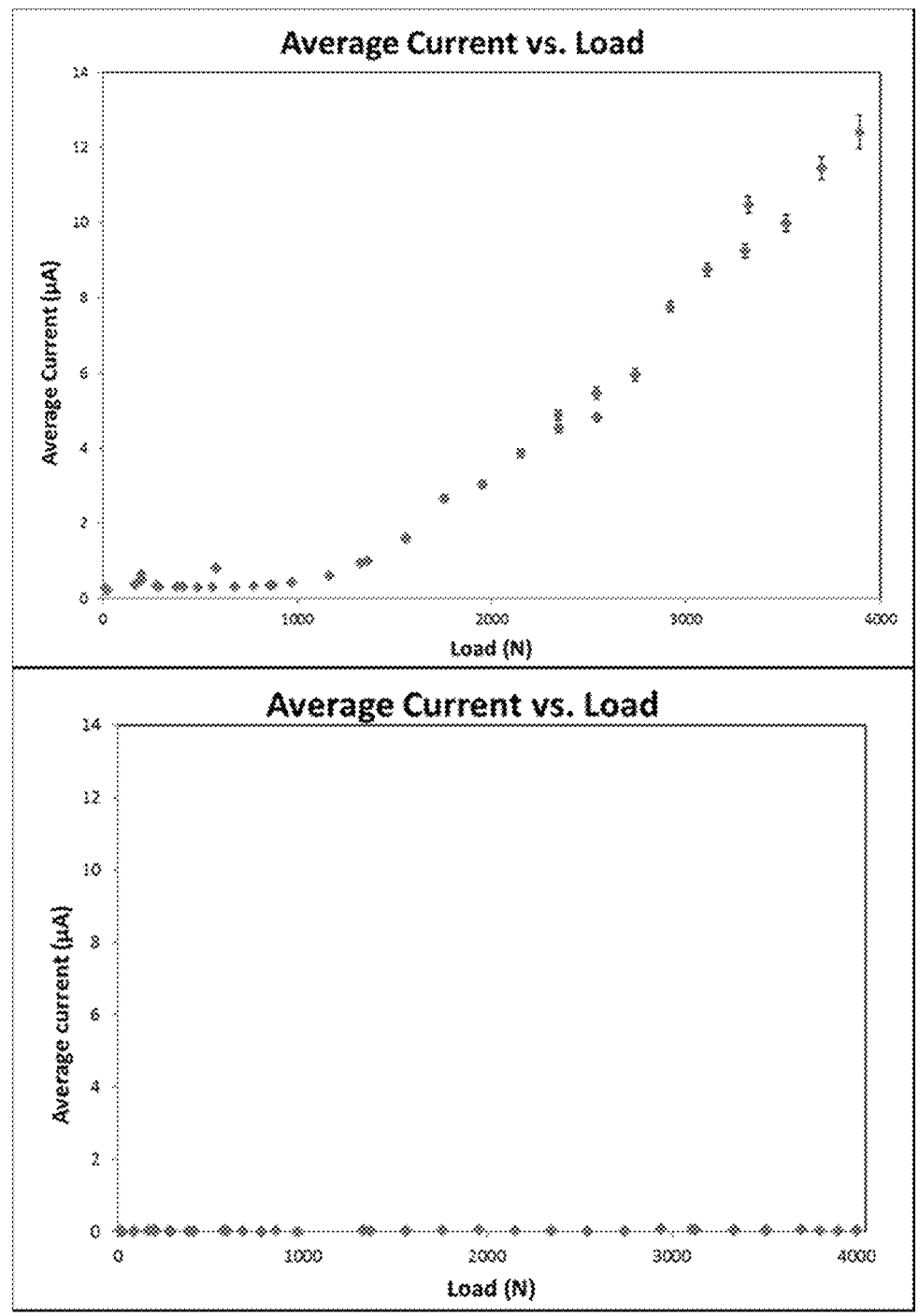
Figure 14:
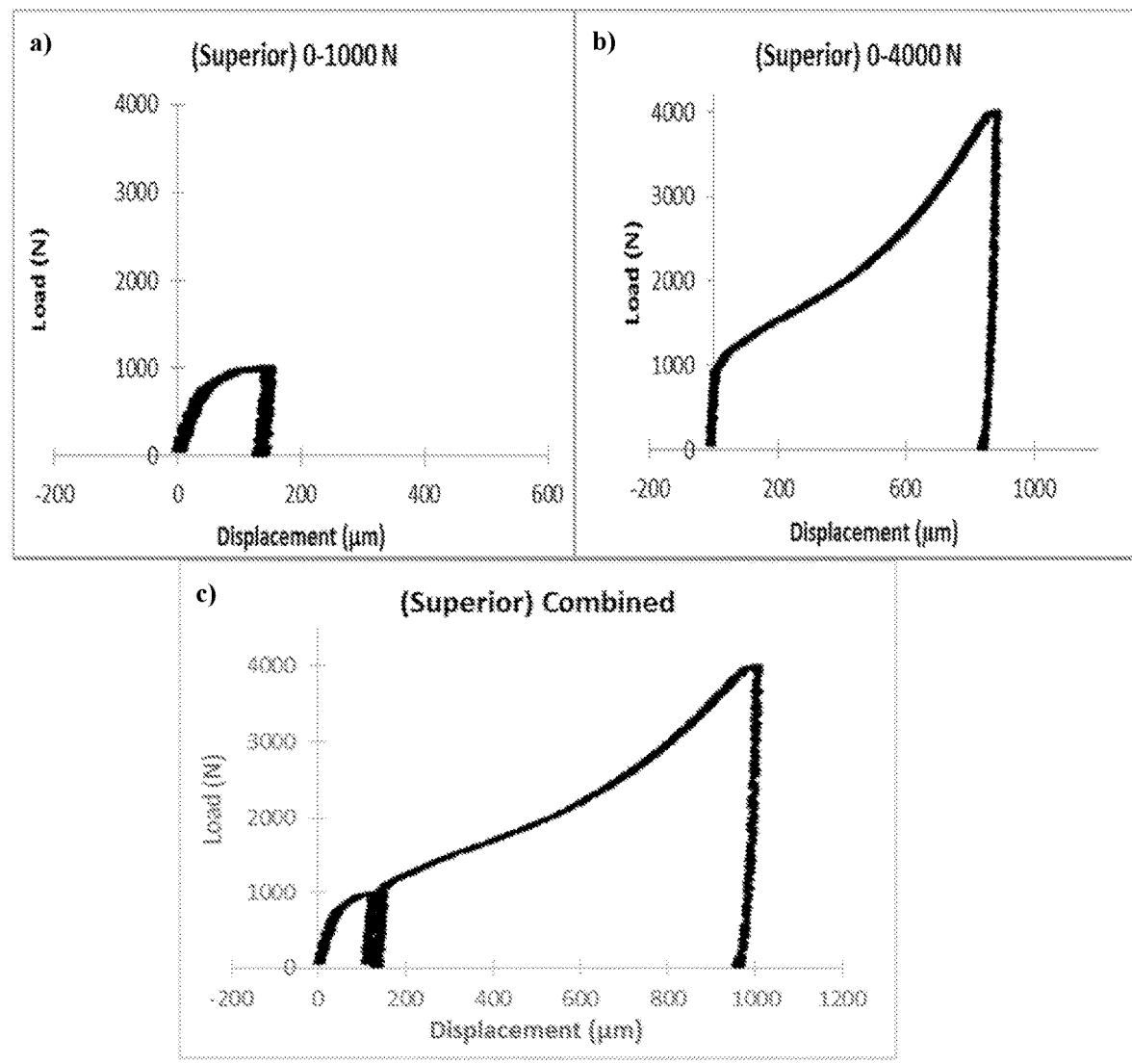

FIG. 4 is a seating schematic of dry assembled and contaminated taper junction. The initial contact point of the trunnion is higher in the contaminated schematic. The contaminated junction also highlights uneven seating of the head, with higher seating displacement in the inferior compared to the superior (canted seating);

FIG. 5 is a series of graphs of seating load-displacement illustrating slip phenomenon in solid contaminant sample. Slipping accounted for a large amount of seating displacement;

FIG. 6 is a series of graphs of average seating displacement data per group (n=5) showed in the superior sensor the wet group had the lowest amount of seating compared to the remaining groups ($P<0.05$) The solid contaminants had the highest amount of seating;

FIG. 7 is a series of graphs of average work of seating per group (n=5). In the superior sensor the wet group had the lowest amount of work of seating compared to the remaining groups ($P<0.05$) The solid contaminants had the highest amount of work;

FIG. 8 is a series of graphs of (a) Average micromotion and (b) subsidence per group at 4000 N. The data shows the dry group had the lowest amount of micromotion at the end of testing ($P<0.05$);

FIG. 9 is a series of graphs of average (a) onset load and (b) current at 4000 N. These plots show the solid lipids group required a significantly larger load to commence current and had no current at the end of testing ($P<0.05$);

FIG. 10 is a graph of average pull-off force per group (n=5) showed the wet group required the lowest load to be pulled off ($P<0.05$). The remaining groups were not different;

FIG. 11 is a series of graphs of subsidence and micromotion vs. time of bone chip sample. The plots show the subsidence of the head onto the neck and corresponding micromotion for both sensors;

FIG. 12 is a series of graphs of subsidence and micromotion vs. time of solid fat sample. The plots show the subsidence of the head onto the neck and corresponding micromotion for both sensors;

FIG. 13 is a series of graphs of average current vs. load of the (a) bone chip and (b) solid lipid samples. The plots show the increase in average current throughout testing in the bone chip sample. However, there is no increase in the average current in the solid lipids sample;

FIG. 14 is a series of graphs of seating load-displacement for a bone chip model. These graphs show a limitation in the working range of the sensors.

DETAILED DESCRIPTION OF THE INVENTION

Figure 1:
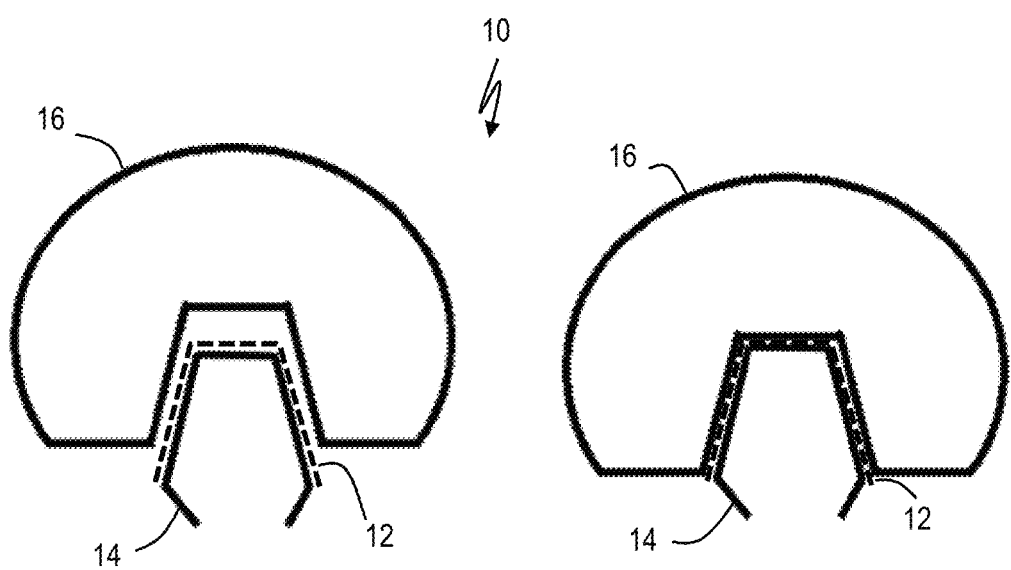
FIG. 1 is a seating schematic of a taper junction having a lipid layer according to the present invention.

Referring to the figures, wherein like numerals refer to like parts throughout, there is seen in FIG. 1 a modular orthopedic implant 10 treated according to the present invention to prevent fretting corrosion. More specifically, a layer of a lipid 12 is applied over the male portion 14, shown as the conical male trunnion of a hip implant, prior to insertion into the female portion 16, shown as the female ball portion of a hip implant. Lipid 12 may comprise porcine lipid or any conventional lipid source and is applied evenly over male portion 14 prior to insertion so that the entire taper junction between male portion 14 and female portion 16 includes lipid 12. Lipid 12 is preferentially a liquid at room temperature, but may be solid instead.

As explained below, various testing established that the approach of the present invention provides benefits, including improved taper locking and reduced fretting corrosion. More specifically, testing provided evidence that applying a lipid coating to the male portion of the trunnion may increase seating displacement, reduce fretting corrosion current, and increase taper stability. Lipids were shown to increase both the seating displacement as well as the pull-off load and the introduction of lipids into the taper junction increased the onset load and reduced (and in some instances eliminated) fretting corrosion current. The introduction of lipids to the taper junction of sample implants significantly altered the electrochemical results. The lipid treated sample implants also required larger loads to initiate fretting corrosion and, in many cases, corrosion was entirely mitigated.

Example 1

In this experiment, 12/14 modular tapers were contaminated with liquid solution, fresh porcine lipids (both solid and liquid) and bovine bone chips. The goal of this study was to assess the effects of a range of solid and liquid substances on seating load-displacement mechanics and correlate these to taper locking stability.

Ti6Al4V 12/14 tapers with CoCrMo heads were axially seated to 4000 N. Samples were divided into five test groups (n=5): dry (control), wet, liquid porcine lipids/fat, solid lipids/fat and bone chip. Wet trunnions were immersed in a 10% fetal bovine serum and phosphate buffered saline solution. Liquid lipid trunnions were thinly coated in lipids rendered from porcine fat, while solid lipids of approximately 3 mm×3 mm were directly placed on the male superior portion of the trunnion. Lastly, bone chip models approximately 45-50 μm in thickness and about 2 mm×2 mm across were positioned on the male trunnion in a superior location at approximately the mid-point of the taper length.

Samples were positioned directly under a load applicator and sensors were fixed thereto. Solid contaminants were placed on the superior portion of the male taper. Reported seating displacements were defined as the distance traveled from 100 N to unload in order to normalize the results. Statistical analysis was performed using an ANOVA test (P<0.05).

Figure 2A:
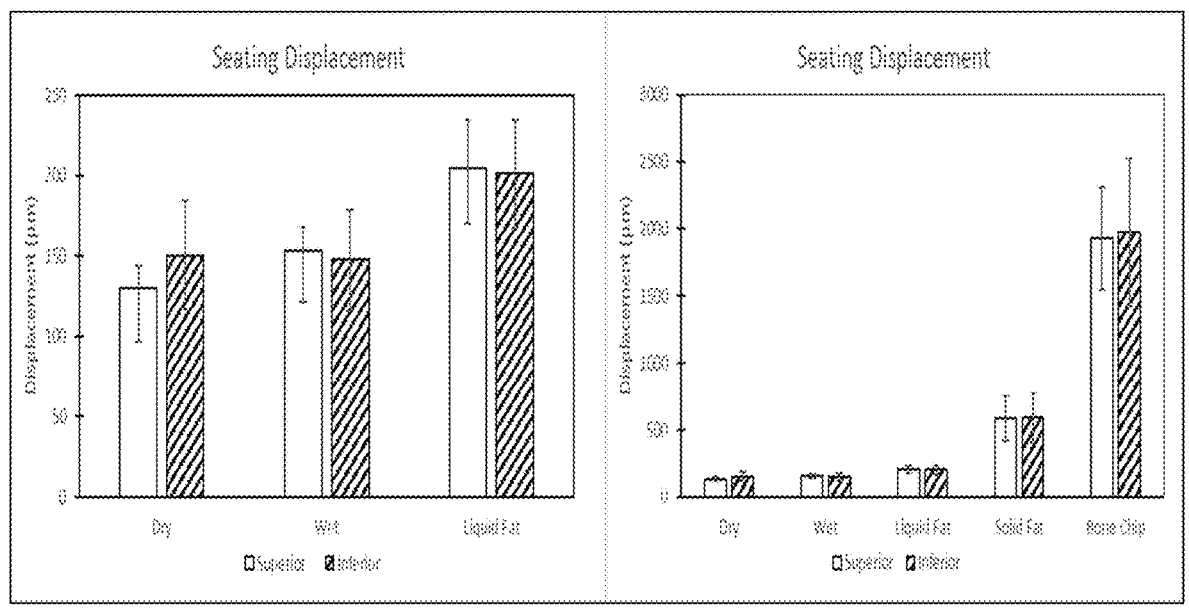
FIG. 2A is series of graphs of average seating displacement per group (n=5). Each group was statistically different with the lowest displacement in the dry group and the greatest in the bone chip group ($P<0.05$)

Summarized seating displacement data shows there was a statistically significant difference in the seating displacement for all groups (FIG. 2A). The dry group had the lowest displacement (P<0.05) while the displacement was greatest in the solid contaminants group (solid lipid and bone chip). The inferior displacement was not different between the dry and wet groups (FIG. 2A).

Figure 2B:
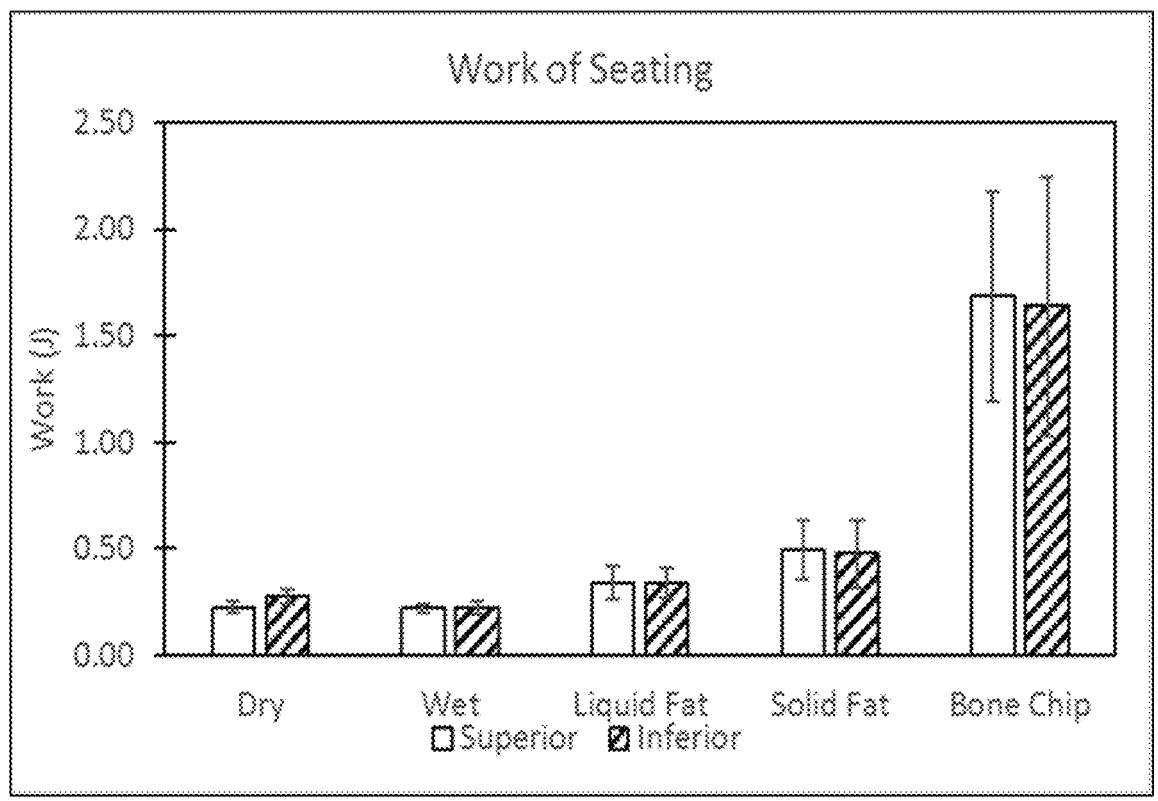
FIG. 2B is a graph of average work of seating per group showed the bone chip group had the greatest work of seating ($P<0.05$), the dry and wet groups recorded the lowest.

The work of seating (FIG. 2B) was highest for the bone chip contamination group, followed by the solid and liquid fat groups (P<0.05). There was no difference between the dry and wet groups. The work to seat a taper with a bone chip was about 4 to 5 times the work to seat a clean and dry taper.

The pull-off load after testing (FIG. 3) shows the liquid fat and bone chip groups required significantly greater pull-off loads than the other groups (P<0.05). The remaining groups weren't different. For some of the liquid fat tapers, the pull-off load was as great as, or greater than the initial seating load.

The effects of the substances on the static seating and pull-off behavior of contaminated taper junctions simulating surgical scenarios were quantitatively studied in an instrumented seating and pull-off test. After quantitative measurement of seating, pull-off loads were captured to measure taper locking stability. The introduction of solid substances to the taper junction significantly altered the seating mechanics (seating load-displacement behavior and work of seating). FIG. 4A illustrates dry taper assembly, the head engages with the neck at a lower point and the superior and inferior portion seat equally. In FIG. 4A, the head engages considerably higher due to the solid contaminant.

As the load is applied the non-contact sensors recorded larger displacements which are required to overcome the presence of the contaminant and reach the final seating displacement point. The schematic also demonstrates the canting behavior caused by solid contaminants leading to varied seating between the superior and inferior sensors. The inferior sensor recorded 10-40 μm of greater seating displacement on average than the superior in the solid groups. The seating load-displacement behavior of a solid contaminant sample also captures a slipping phenomenon captured by both sensors at a low load level (FIG. 5). This slipping is the result of crushing and spreading of the solid contaminant into the constrained taper gap region. In the solid fat samples during slipping, there is a rendering of the solid fat into liquid which is then distributed about the taper gap. The slipping, caused by the contaminant, accounts for a large amount of the seating displacement captured during testing.

After slipping the head-neck taper begins to engage and lock at the max load. After testing, the bone chip and solid fat contaminants were highly deformed and compressed in the taper gap region.

Figure 3:
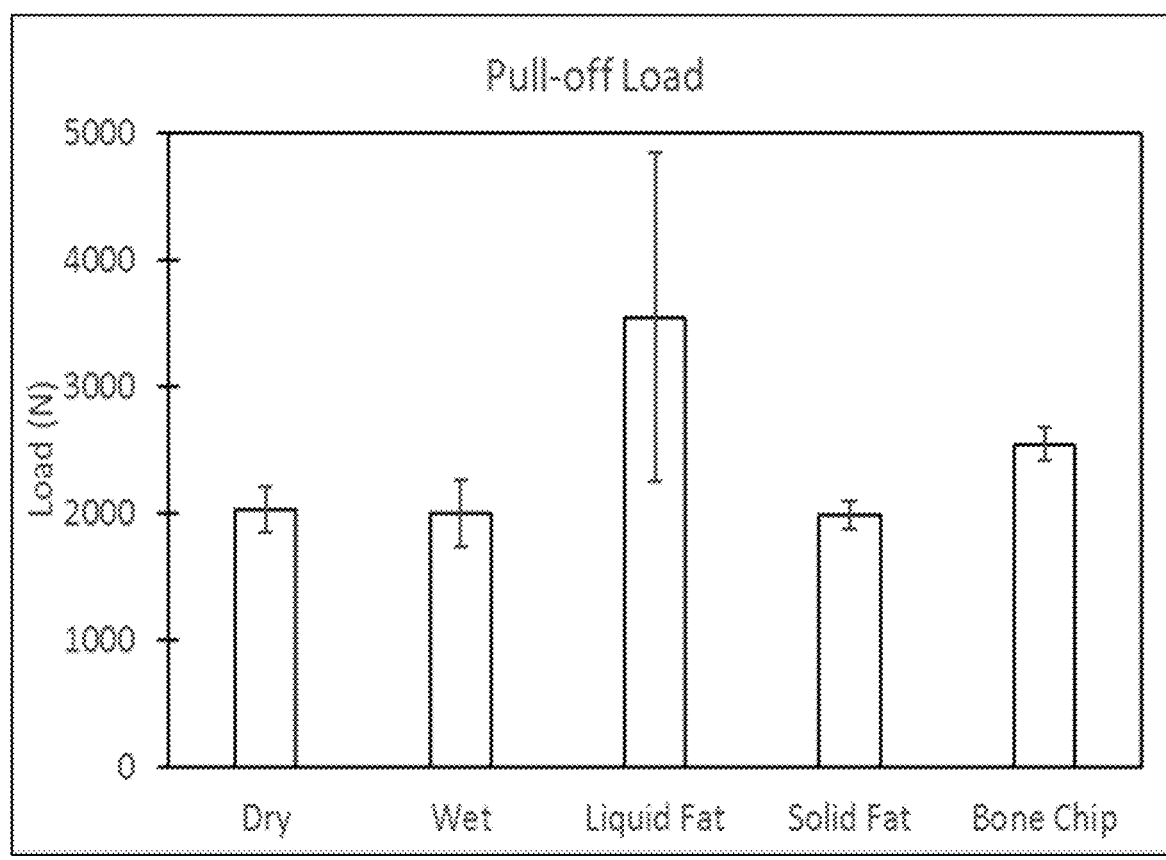
FIG. 3 is a graph showing that the liquid fat group recorded a significantly greater average pull-off load than the remaining groups ($P<0.05$). In select instances the pull-off load of certain samples was a great, or greater than the seating load.

Post seating, the pull-off loads were calculated and plotted in FIG. 3. Pull-off load values, used to assess the stability of the taper, are typically half the seating load depending on the taper geometry, coefficient of friction, etc. In this study, liquid fat samples on average recorded higher pull-off loads than three of the four remaining groups with an average pull-off load of 3500 N. In some instances, the liquid fat samples recorded values greater than the initial seating load. These findings indicate liquid fat increased taper stability during testing. The exact reasoning for this is not entirely understood but the liquid fat in the junction could have acted as a lubricant increasing the seating displacement versus the dry group leading to increased taper stability. The fat would then be squeezed out of the junction due to loading with the coagulated buildup of the liquid lipids showing at the bottom of the trunnion, which led to the previous assumption.

Testing was completed on the same servohydraulic system using the same sensors but was still subject to certain limitations. The samples during axial loading could have toggled and/or rocked off-axis which would not be accurately read in the two sensor configuration. The exact dimensions of each contaminant was closely controlled but still may have had some variability which may have led to variability during testing.

This study compared the influence of contamination (wet, lipids and bovine bone) at the taper junction on seating mechanics compared to control (dry) samples in 12/14 Ti6Al4V/CoCrMo trunnions. The introduction of contaminants significantly increased the measured seating displacement of the head on the neck as well as the work of seating. The solid contaminants (solid lipids and bone chip) recorded the greatest seating displacement and work of seating. Taper locking stability testing showed the introduction of liquid lipids significantly increased the pull-off load, approximately 89% of the seating load. Testing also showed solid contaminants may increase canted seating of the head (i.e. increased seating displacement of one portion of the head compared to the other)

Example 2

In this experiment, 12/14 modular tapers were contaminated with a liquid solution, fresh porcine lipid, and bovine bone chips and analyzed for fretting corrosion. The fretting data, both fretting motions and fretting current, were concurrently captured during short-term incremental cyclic fretting corrosion tests. The goals of this experiment were to assess the effects of each contaminant on incremental cyclic fretting corrosion (ICFC) behavior and micromotions during testing. Pull-off loads were captured post cyclic testing.

Ti6Al4V 12/14 tapers and CoCrMo heads were axially seated to 4000 N in five contamination groups (n=5): dry, wet, liquid porcine lipids (liquid fat), solid lipids (solid fat) and bone chip. Trunnions were thinly coated in liquid lipids, while solid lipid trunnions had the contaminant placed on the male superior portion of the trunnion. Wet trunnions were immersed in a 10% fetal bovine serum and phosphate buffered saline solution. Lastly, bone chip models were approximately 45-50 μm in thickness and 2×2 mm across and positioned on the male superior portion. A tensile pull-off load was applied (5 mm/min) until the taper junction failed and the head-neck disassembled. An ANOVA test (P<0.05) was used for statistical comparisons between groups. Results reported in this section are comprised of rigid body motion data only.

The seating load-displacement behavior for the sample groups showed the control group as well as the liquid contamination groups had a statistically lower seating displacement compared to the solid contamination groups. The superior portion of the wet group had a statistically lower seating displacement compared to the control (FIG. 6) (P<0.05). Similarly, the work of seating for the wet group on the superior portion was lower than all other groups while work of seating for both sensors was highest in the solid contamination groups (FIG. 7) (P<0.05). FIG. 8 summarizes the micromotion (FIG. 8a) and subsidence (FIG. 8b) for the different test groups.

During cyclic loading, all samples showed levels of micromotion and subsidence. However, the dry control group maintained lower levels of micromotion throughout testing, the other groups were not statistically different from one another (P<0.05). The inferior portion of the wet samples experience more negative subsidence, further seating of the head onto the neck, than the dry samples. The reported subsidence of the other groups was not different (P<0.05)

The onset load for fretting corrosion showed the two lipid groups required higher loads before the current deviated from the baseline (P<0.05). There was no difference between the remaining groups (FIG. 9a). The solid fat group had the lowest reported fretting currents at 4000 N opposite that of the bone chip group which had the highest currents on average (FIG. 9b) (P<0.05). The liquid fat had highly variable results as can be seen by the large standard deviation indicating that some currents were low and some were very high.

The pull-off loads captured after cyclic testing, shown in FIG. 10, show the wet group required the lowest amount of force to distract the head (P<0.05). The remaining groups were not different with an average approximate force of 2500 N.

The effects of incremental cyclic fretting corrosion testing of contaminated head-neck taper junctions simulating surgical scenarios were quantitatively studied in an instrumented cyclic test method. Taper contaminants caused variations in seating load-displacement behavior, micromotion and subsidence as well as fretting corrosion behavior during cyclic loading. The information in this study can be used to better understand the role of contamination on fretting motions and subsequent fretting corrosion.

Subsidence data showed more negative subsidence on the superior portion of the solid contamination groups which could indicate that the contaminants required larger amounts of angled force to be negated. After being ground down, they no longer obstruct the seating motion and when overcome the head sat further down on that portion. The plots in FIG. 11 illustrate a significant change in both the subsidence and micromotion at about 4000 s in a bone chip sample. At approximately 2800 N the assumption can be made the load overcame the bone chip and upon continued cyclic loading the head seated further onto the neck increasing the subsidence and micromotion.

FIG. 12 illustrates the same behavior shown in the previous figure, where the solid lipid contaminant is overcome at about 3000 s which leads to a large subsidence and increase in micromotion.

Yet despite the similarities in the two load-displacement plots throughout the course of testing, the solid lipids group displayed a unique phenomenon. As the micromotion and subsidence increase due to the contaminants, the current in the solid lipid group does not deviate from the baseline while the bone chip current rapidly rises with the increase in loud (FIG. 13).

Data from testing suggests the fat was overcome and extruded to the mouth of the junction creating a hydrophobic seal around the opening of the junction preventing the ingress of liquid which inhibited the fretting corrosion process. The fat created a seal of sorts around the base of the junction which altered the fretting corrosion response.

Testing was subject to a few limitations. Sensors were only able to capture up to 1 mm of displacement but during the seating of solid contaminant groups, the displacement exceeded the sensing range. To overcome the limitation, the samples were loaded from 0 to 1000 N, the sensors were then repositioned and the samples were loaded from 0 to 4000 N. Displacement was captured for both loading sequences (FIG. 14a and FIG. 14b). FIG. 14c demonstrates how the two plots were combined, the displacement from the 0-4000 N seating test was shifted to align with the end of the 0-1000 N test. The final seating displacement and work of seating could then be calculated.

Positioning of the sensors also led to limitations. The sensors were able to capture positioning, toggling and rotation about one-axis but were not able to capture torsion which could have been amplified due to the contaminants. Lastly, a weakness of this study was the large seating load (4000 N) was used to seat the tapers. It is likely a surgeon who induces significant contamination may also be likely to not seat the taper to as large a seating force as studied in this work.

In conclusion, the incorporation of certain substances to the head-neck taper junction not only led to increased seating displacement and work of seating but increased micromotion and subsidence during cyclic loading as well. Data from testing, however, suggests that the incorporation of lipids or a lipid-like substrate which accumulates about the mouth of the taper junction will increase the onset load and decrease the amount of corrosion at the end of testing. The incorporation of lipids also increased the pull-off load necessary to separate the head from the neck. There was no difference between the remaining groups ($P<0.05$).

It should be recognized that the testing protocol explained herein could be used to identify additional compounds or substances that protect against corrosion. For example, hydrophobic organic (or polymeric) materials that provide similar functionality to the lipids that were tested may also provide the same benefits. One function provided by hydrophobic materials, such as the present lipids, may provide is the prevention of the ingress of aqueous fluids into the crevice, thereby preventing the negative electrochemical processes from occurring as an aqueous electrolyte is needed in order to have corrosion processes taking place.

What is claimed is:

1. A modular orthopedic interface, consisting of:
   a male portion;
   a female portion coupled to the male portion by a taper junction; and
   a hydrophobic lipid positioned in the taper junction between the male portion and the female portion.

2. The implant of claim 1, wherein the lipid comprises porcine lipid.

3. The implant of claim 1, wherein the lipid is liquid.

4. The implant of claim 1, wherein the male portion comprises a neck of a hip implant and the female portion comprises a head of the hip implant.

5. The implant of claim 4, wherein the male portion and the female portion are formed from Ti6Al4V.

6. The implant of claim 1, wherein an amount of force required for separation of the male portion and the female portion is at least fifty percent greater than in an identical implant lacking the lipid positioned in the taper junction.

* * * * *